US011385206B2

(12) United States Patent
Hanafusa

(10) Patent No.: US 11,385,206 B2
(45) Date of Patent: Jul. 12, 2022

(54) PREPROCESSING APPARATUS AND ANALYSIS SYSTEM COMPRISING THE PREPROCESSING APPARATUS

(71) Applicant: SHIMADZU CORPORATION, Kyoto (JP)

(72) Inventor: Nobuhiro Hanafusa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 140 days.

(21) Appl. No.: 17/009,302

(22) Filed: Sep. 1, 2020

(65) Prior Publication Data

US 2020/0393424 A1 Dec. 17, 2020

Related U.S. Application Data

(62) Division of application No. 15/905,954, filed on Feb. 27, 2018, now abandoned.

(30) Foreign Application Priority Data

Mar. 3, 2017 (JP) .............................. JP2017-040356

(51) Int. Cl.
*G01N 30/06* (2006.01)
*G01N 1/28* (2006.01)
(Continued)

(52) U.S. Cl.
CPC ............... *G01N 30/06* (2013.01); *B01L 3/502* (2013.01); *G01N 1/28* (2013.01); *G01N 1/40* (2013.01);
(Continued)

(58) Field of Classification Search
None
See application file for complete search history.

(56) References Cited

U.S. PATENT DOCUMENTS 4,859,605 A 8/1989 Metzger et al.
2011/0157580 A1 6/2011 Nogami et al.
(Continued)

FOREIGN PATENT DOCUMENTS

EP 2490019 A1 8/2012
JP 2010-060474 A 3/2010
(Continued)

OTHER PUBLICATIONS

Communication dated Jul. 19, 2018, from the European Patent Office in counterpart European Application No. 18000194.3.
(Continued)

*Primary Examiner* — Kathryn Wright
(74) *Attorney, Agent, or Firm* — Sughrue Mion, PLLC

(57) ABSTRACT

Disclosed herein is a preprocessing apparatus that makes it possible to highly efficiently analyze specimens held by solid media, such as dried blood spots to be used for newborn mass screening or the like. The preprocessing apparatus includes: a preprocessing container setting part in which a preprocessing container containing a solid sample including a specimen to be analyzed and a solid medium holding the specimen is to be set; a carrying mechanism that carries the preprocessing container set in the preprocessing container setting part; and a preprocessing part that has a port for setting the preprocessing container carried by the carrying mechanism and that is configured to perform preprocessing including extraction processing for extracting the specimen from the solid sample contained in the preprocessing container set in the port.

3 Claims, 17 Drawing Sheets

(51) Int. Cl.
*G01N 1/40* (2006.01)
*G01N 33/49* (2006.01)
*G01N 35/00* (2006.01)
*G01N 35/04* (2006.01)
*B01L 3/00* (2006.01)
*G01N 35/10* (2006.01)
*G01N 30/00* (2006.01)
*G01N 30/02* (2006.01)

(52) U.S. Cl.
CPC .......... *G01N 1/4005* (2013.01); *G01N 33/49* (2013.01); *G01N 35/00584* (2013.01); *G01N 35/04* (2013.01); *B01L 2200/0631* (2013.01); *B01L 2300/0681* (2013.01); *B01L 2400/049* (2013.01); *G01N 1/405* (2013.01); *G01N 35/10* (2013.01); *G01N 2001/288* (2013.01); *G01N 2001/4011* (2013.01); *G01N 2030/009* (2013.01); *G01N 2030/027* (2013.01); *G01N 2030/062* (2013.01); *G01N 2035/00485* (2013.01); *G01N 2035/00524* (2013.01); *G01N 2035/0441* (2013.01); *G01N 2035/0443* (2013.01)

(56) References Cited

U.S. PATENT DOCUMENTS

| | | |
|---|---|---|
| 2012/0121464 A1 | 5/2012 | Nogami et al. |
| 2012/0134895 A1 | 5/2012 | Kanda et al. |
| 2012/0206713 A1 | 8/2012 | Nogami et al. |
| 2014/0366656 A1 | 12/2014 | Brousmiche et al. |
| 2017/0168027 A1* | 6/2017 | Hanafusa ............... G01N 30/06 |
| 2017/0269112 A1 | 9/2017 | Gerstel |
| 2017/0284982 A1 | 10/2017 | Hanafusa et al. |
| 2018/0196016 A1 | 7/2018 | Hanafusa et al. |

FOREIGN PATENT DOCUMENTS

| | | | |
|---|---|---|---|
| JP | 2014-526710 A | 10/2014 | |
| JP | 2016-170079 A | 9/2016 | |
| WO | 2016/017042 A1 | 2/2016 | |
| WO | 2016016109 A2 | 2/2016 | |
| WO | WO-2016017042 A1 * | 2/2016 | ............... G01N 1/10 |
| WO | 2016/035139 A1 | 3/2016 | |
| WO | 2017006476 A1 | 1/2017 | |

OTHER PUBLICATIONS

Japanese Office Action issued in JP 2017-040356 dated Jul. 3, 2020.
Communication dated Feb. 10, 2021 from the European Patent Office in Application No. 18000194.3.

* cited by examiner

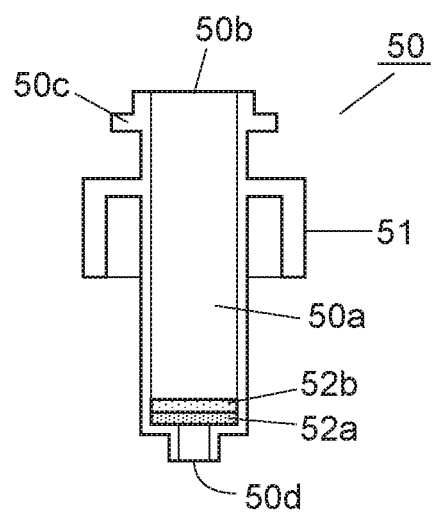

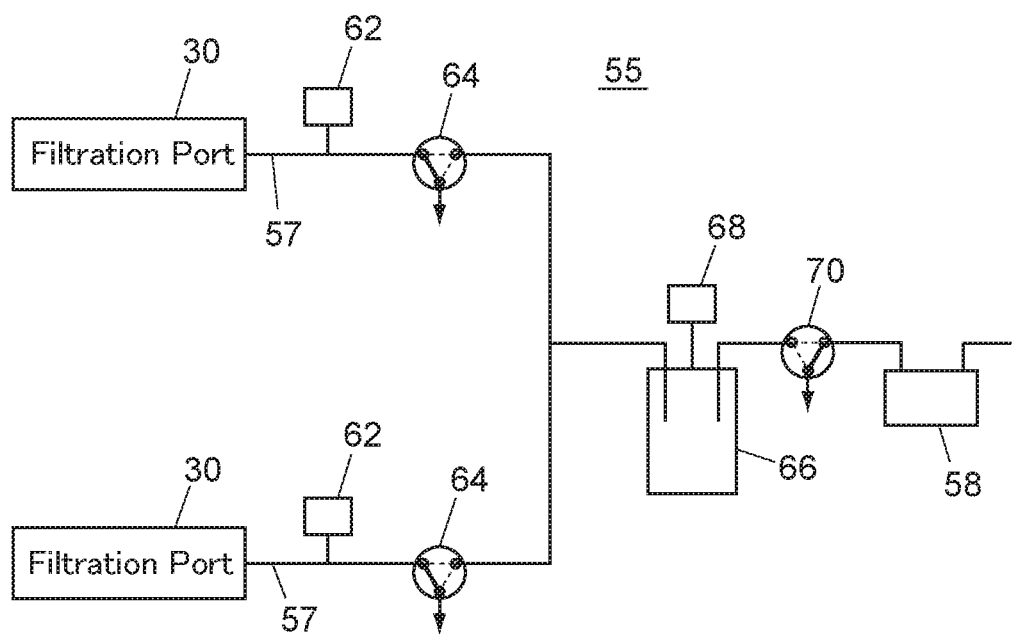

PREPROCESSING APPARATUS AND ANALYSIS SYSTEM COMPRISING THE PREPROCESSING APPARATUS

CROSS-REFERENCE TO RELATED APPLICATIONS

This application is a divisional of U.S. patent application Ser. No. 15/905,954, filed Feb. 27, 2018, which claims priority to Japanese Patent Application No. 2017-040356, filed Mar. 3, 2017, the disclosures of which are incorporated herein by reference in their entireties.

BACKGROUND OF THE INVENTION

1. Field of the Invention

The present invention relates to a preprocessing container for performing preprocessing such as extraction processing for extracting, as a sample, necessary components contained in a living body-derived sample such as whole blood, blood serum, blood plasma, dried blood spot, or urine by removing a specific component unnecessary for analysis from the living body-derived sample, a preprocessing apparatus that automatically performs preprocessing using the preprocessing container, and an analysis system that comprises the preprocessing apparatus and automatically performs a series of processes from preprocessing of a sample to analysis.

2. Description of the Related Art

When the quantitative analysis of a sample such as a biological sample is performed, there is a case where it is necessary to perform processing for extracting necessary components as a sample by removing a specific component unnecessary for analysis from the biological sample or drying/solidifying processing for concentrating or drying/solidifying an extracted sample. Various preprocessing apparatuses that automatically perform such preprocessing have heretofore been proposed and practically used (see, for example, JP 2010-60474 A).

For example, JP 2010-60474 A discloses that a plurality of cartridges holding a separating agent that separates a specific component by allowing a sample to pass therethrough are held by a common carrying mechanism, these cartridges are sequentially placed in a pressure applying mechanism provided in a predetermined position by the carrying mechanism, and pressure is applied to each of the cartridges in the pressure applying mechanism to perform sample extraction. In this case, a plurality of extract receivers that receive extracts from the cartridges are moved relative to the cartridges below the cartridges by a carrying mechanism different from the carrying mechanism for cartridges so that the receivers are sequentially placed in the pressure applying mechanism to continuously perform sample extraction.

However, in the case of the above-described system, the carrying mechanism for cartridges and the carrying mechanism for extract receivers cannot be moved while sample extraction processing is performed in the pressure applying mechanism, and therefore there is a limit to improving preprocessing efficiency. Therefore, the present inventor has proposed that a set of a separation device having a filter for filtering a sample and a collection container for collecting an extracted sample discharged from the separation device is carried in a random access manner to a port where processing such as filtration processing or stirring processing is performed to improve preprocessing efficiency (see WO 2016/017042 A1 and JP 2016-170079 A).

SUMMARY OF THE INVENTION

The analysis of dried blood spots, such as newborn mass screening, is generally performed in batch mode by placing dried blood spots in wells of a plate having a plurality of wells, such as a 96-well plate. However, such a batch mode analysis is poor in operation efficiency and has high running costs unless a fairly large number of specimens are analyzed. Further, it is necessary to perform preprocessing sequentially from the first specimen, and therefore, there is a time lag between the preprocessing of the first specimen and the preprocessing of the last specimen, which impairs the accuracy of analysis.

Further, in such a batch mode analysis method as described above, specimen management and preprocessing such as reagent dispensing are manually performed, and therefore, problems such as mix-up of specimens and variation in the amount of a reagent dispensed, are likely to occur. In order to overcome such problems, it is desired that dried blood spots be automatically and more efficiently analyzed.

It is therefore an object of the present invention to make it possible to highly efficiently analyze specimens held by solid media, such as dried blood spots to be used for newborn mass screening or the like.

The present invention is directed to a preprocessing apparatus comprising: a preprocessing container setting part where a preprocessing container containing a solid sample comprising a specimen to be analyzed and a solid medium holding the specimen is to be set; a carrying mechanism that carries the preprocessing container set in the preprocessing container setting part; and a preprocessing part that has a port for setting the preprocessing container carried by the carrying mechanism and that is configured to perform preprocessing including extraction processing for extracting the specimen from the solid sample contained in the preprocessing container set in the port.

Here, the solid sample refers to a sample in which a specimen is held by a solid medium. In the present invention, the term "solid medium" refers to a medium having the function of holding a liquid material or a dried and solidified liquid material in or on its membrane, such as filter paper, cotton, gauze, a PTFE (polytetrafluoroethylene) membrane, a nylon membrane, a polypropylene membrane, a PVDF (polyvinylidene fluoride) membrane, an acrylic copolymer membrane, a mixed cellulose membrane, a nitrocellulose membrane, a polyethersulfone membrane, an ion-exchange membrane, or a glass fiber membrane. Examples of the specimen to be held by such a solid medium include living body-derived specimens such as whole blood, blood serum, urine, and saliva.

It is preferred that the preprocessing container setting part is configured to allow an empty preprocessing container containing no specimen to be also set therein, and the preprocessing apparatus further comprises a specimen setting part where a specimen container containing a liquid specimen is to be set, a specimen dispensing part that takes the specimen from the specimen container set in the specimen setting part and dispenses the specimen into the empty preprocessing container placed in a predetermined dispensing position, and a specimen recognition part that checks whether a specimen to be analyzed is a liquid specimen or a specimen contained in the solid sample. This makes it possible to perform not only preprocessing of a specimen contained in the solid sample but also preprocessing of a liquid specimen.

In this case, it is preferred that the preprocessing apparatus further comprises a preprocessing operation part that is configured to, when the specimen recognition part recognizes that a specimen to be analyzed is a liquid specimen, allow the carrying mechanism to carry the empty preprocessing container set in the preprocessing container setting part to the dispensing position, allow the specimen dispensing part to dispense the specimen to be analyzed into the preprocessing container, and then allow the carrying mechanism to carry the preprocessing container to the preprocessing part to perform predetermined preprocessing, and that is configured to, when the specimen recognition part recognizes that a specimen to be analyzed is a specimen contained in the solid sample, allow the carrying mechanism to carry the preprocessing container containing the solid sample and set in the preprocessing container setting part to the preprocessing part to perform predetermined preprocessing including the extraction processing.

It is preferred that the preprocessing part has a plurality of extraction ports for performing the extraction processing, and the preprocessing operation part is configured to, when the specimen recognition part recognizes that a specimen to be analyzed is a specimen contained in the solid sample, search the available extraction port and allow the carrying mechanism to carry the target preprocessing container to the available extraction port to perform the extraction processing. This makes it possible to, when there is an available extraction port, carry the preprocessing container to the available extraction port to perform specimen extraction processing in a random access manner, which improves preprocessing efficiency.

It is preferred that the preprocessing container setting part is configured to allow a plurality of preprocessing containers to be set therein, and the preprocessing apparatus further comprises a solid sample setting information holding part that holds information about a position where the preprocessing container containing the solid sample is set in the preprocessing container setting part and a preprocessing container identification part configured to, when a specimen to be analyzed is a specimen contained in the solid sample, identify the preprocessing container containing the solid sample containing the specimen on a basis of the information held in the solid sample setting information holding part. This makes it possible to previously register the position of the preprocessing container containing the solid sample on the solid sample setting information holding part so that the position of the preprocessing container containing the solid sample can be automatically identified, the target preprocessing container can be carried to the preprocessing part by the carrying mechanism, and preprocessing of a specimen contained in the solid sample can be automatically performed.

The present invention is also directed to an analysis system comprising: the above-described preprocessing apparatus including a transfer device that has a transfer port where the preprocessing container containing a specimen that has been subjected to preprocessing in the preprocessing part is to be set by the carrying mechanism and that is configured to move the transfer port to transfer the container set in the transfer port to an outside of the preprocessing apparatus; and a liquid chromatographic system that is provided adjacent to the preprocessing apparatus and that has an analytical flow path that allows a mobile phase to flow therethrough, a sample injector that takes, as a sample, the specimen contained in the container moved to the outside of the preprocessing apparatus by the transfer device and injects the sample into the analytical flow path, an analytical column provided on the analytical flow path to separate the sample injected by the sample injector into individual components, and a detector that detects the sample components separated by the analytical column.

The preprocessing apparatus according to the present invention comprises: a preprocessing container setting part where a preprocessing container containing a solid sample comprising a specimen to be analyzed and a solid medium holding the specimen is to be set; a carrying mechanism that carries the preprocessing container set in the preprocessing container setting part; and a preprocessing part that has a port for setting the preprocessing container carried by the carrying mechanism and that is configured to perform preprocessing including extraction processing for extracting the specimen from the solid sample contained in the preprocessing container set in the port. This makes it possible to individually and efficiently perform preprocessing of a specimen held by a solid medium such as filter paper regardless of the number of specimens. Since the preprocessing of a specimen is automatically performed in the preprocessing part, errors and variations caused by manual work performed by an analyst are eliminated, and therefore the accuracy of analysis results can be improved.

In the analysis system according to the present invention, a specimen can be subjected to preprocessing in the preprocessing apparatus described above, and then the specimen that has been subjected to preprocessing can be automatically introduced into a liquid chromatographic system to be subjected to a separating analysis. This makes it possible to fully automatically perform a series of processes from the preprocessing of a specimen contained in a solid sample such as dried blood spot to analysis without human intervention. Since the analysis system is operated without human intervention, errors and variations caused by manual work are eliminated, and therefore the accuracy of analysis results is improved.

BRIEF DESCRIPTION OF THE DRAWINGS

FIG. 2D is a cross-sectional view showing another example of the separation device;

FIG. 5 is a schematic flow path configuration diagram showing the configuration of a negative-pressure applying mechanism;

DETAILED DESCRIPTION OF THE INVENTION

Figure 1:
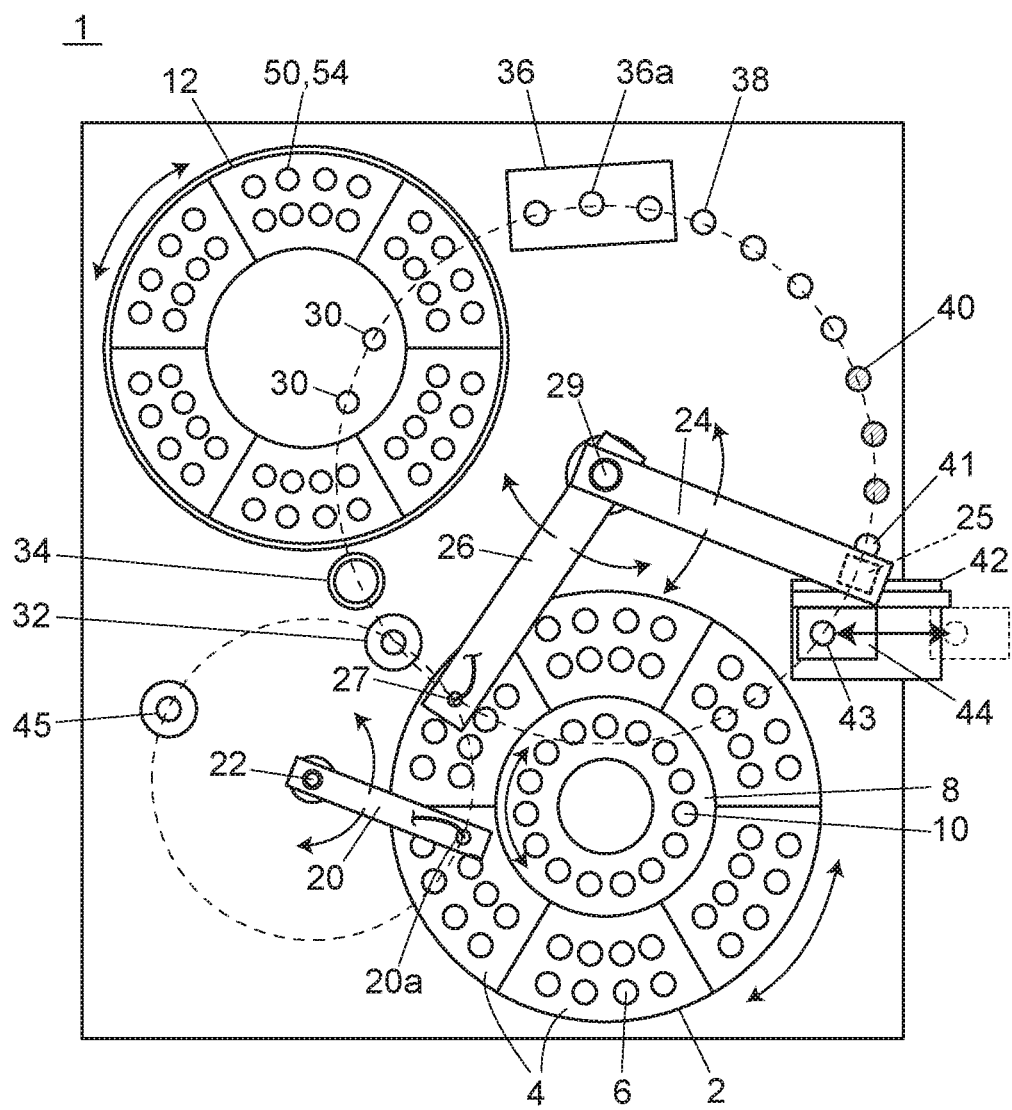
FIG. 1 is a plan view showing an embodiment of a preprocessing apparatus.

An embodiment of a preprocessing apparatus will be described with reference to FIG. 1.

A preprocessing apparatus 1 according to this embodiment performs a necessary preprocessing item with the use of a prepared preprocessing container comprising a set of a separation device 50 and a collection container 54 for each specimen. The preprocessing apparatus 1 has a plurality of processing ports for performing different preprocessing items, and is configured to allow the preprocessing container containing a specimen to be set in any one of the processing ports to perform a preprocessing item corresponding to the processing port on the specimen contained in the preprocessing container. Each of the processing ports will be described later. The preprocessing item refers to the item of preprocessing necessary for performing an analysis item designated by an analyst.

The separation device 50 and the collection container 54 constituting the preprocessing container are carried by a carrying arm 24 constituting a carrying mechanism. The carrying arm 24 has, on its tip side, a holding part 25 for holding the separation device 50 and the collection container 54. The base end of the carrying arm 24 is held by a vertical shaft 29, and therefore the carrying arm 24 rotates about the vertical shaft 29 in a horizontal plane so that the holding part 25 draws an arc-shaped track. All the processing ports and other ports, to which the separation device 50 and the collection container 54 are to be carried, are provided along the arc-shaped track drawn by the holding part 25.

A specimen setting part 2 for setting a specimen container 6 containing a liquid specimen is provided, and a sampling arm 20 is provided adjacent to the specimen setting part 2 as a specimen dispensing part for taking the specimen from the specimen container set in the specimen setting part 2. In the specimen setting part 2, a sample rack 4 for holding the specimen containers 6 is annularly provided. The specimen setting part 2 rotates in a horizontal plane so as to circumferentially move the sample rack 4, and therefore, a desired one of the specimen containers 6 is placed in a predetermined sampling position by the rotation of the specimen setting part 2. The sampling position refers to a position which is along the track of a sampling nozzle 20a provided at the tip of the sampling arm 20 and in which a specimen is taken by the sampling nozzle 20a.

The sampling arm 20 has a base end through which a vertical shaft 22 passes, and therefore rotates about the shaft 22 in a horizontal plane and moves up and down in a vertical direction along the shaft 22. The sampling nozzle 20a is held on the tip side of the sampling arm 20 in such a manner that the tip of the sampling nozzle 20a faces vertically downward, and the sampling nozzle 20a is moved in a horizontal plane so as to draw an arc-shaped track and is moved up and down in a vertical direction by the sampling arm 20.

A dispensing port 32 is provided in a position on the track of the sampling nozzle 20a and on the track of the holding part 25 of the carrying arm 24. The dispensing port 32 is a port where the sampling nozzle 20a dispenses a specimen into the unused separation device 50. The unused separation device 50 is set in the dispensing port 32 by the carrying arm 24. Further, the dispensing port 32 is also used to add a reagent to the separation device 50 containing a specimen or to add a reagent to the separation device 50 containing a solid sample that will be described later.

A reagent setting part 8 for setting a reagent container 10 is provided on the inner side of the specimen setting part 2, and a reagent arm 26 (reagent adding part) for taking a reagent from the reagent container set in the reagent setting part 8 is provided. The base end of the reagent arm 26 is supported by the vertical shaft 29 shared with the carrying arm 24, and therefore, the reagent arm 26 rotates in a horizontal plane and moves up and down. A probe 27 is provided at the tip of the reagent arm 26. The probe 27 is provided in such a manner that its tip faces vertically downward. The probe 27 is moved in a horizontal plane so as to draw the same arc-shaped track as the holding part 25 of the carrying arm 24 and is moved up and down. The proximal end of the probe 27 is connected to a syringe pump that sucks and discharges a liquid so that a reagent is sucked and discharged through the distal end of the probe 27.

The reagent setting part 8 rotates in a horizontal plane independently of the specimen setting part 2. In the reagent setting part 8, the reagent containers 10 are annularly placed. When the reagent setting part 8 rotates, the reagent containers 10 are carried in the direction of rotation of the reagent setting part 8 so that a desired one of the reagent containers 10 is placed in a predetermined reagent taking position. The reagent taking position is a position which is along the track of the probe 27 of the reagent arm 26 and in which a reagent is taken by the probe 27. After sucking a predetermined reagent, the probe 27 dispenses the sucked reagent into the separation device 50 set in the dispensing port 32 to add the reagent to a specimen.

A preprocessing container setting part 12 is provided in a position different from a position where the specimen setting part 2 is provided and from a position where the reagent setting part 8 is provided. The preprocessing container setting part 12 is configured to allow a plurality of preprocessing containers, each of which comprises an unused set of the separation device 50 and the collection container 54 that are stacked, to be annularly set therein. The preprocessing container setting part 12 rotates in a horizontal plane to circumferentially move the preprocessing containers so that any one of the preprocessing containers is placed in a position along the track of the holding part 25 of the carrying arm 24. The carrying arm 24 can hold the unused separation device 50 or collection container 54 placed in a position along the track of the holding part 25.

An analyst may previously set two or more kinds (e.g., two kinds) of the separation devices 50 having separating agents different in separation performance in the preprocessing container setting part 12. These separation devices 50 are selectively used depending on the analysis item of a sample, and an appropriate one of the separation devices 50 is selected by the preprocessing container setting part 12 depending on an analysis item designated by the analyst. The selection of an appropriate one of the separation devices 50 is performed by a controller that controls the operations of the preprocessing apparatus 1. The controller will be described later. The term "analysis item" used herein refers to the kind of analysis to be performed successively using a sample that has been subjected to preprocessing in the preprocessing apparatus 1. Examples of an analyzer that performs such an analysis include a liquid chromatograph (LC) and a liquid chromatograph-mass spectrometer (LC/MS).

Figure 3A:
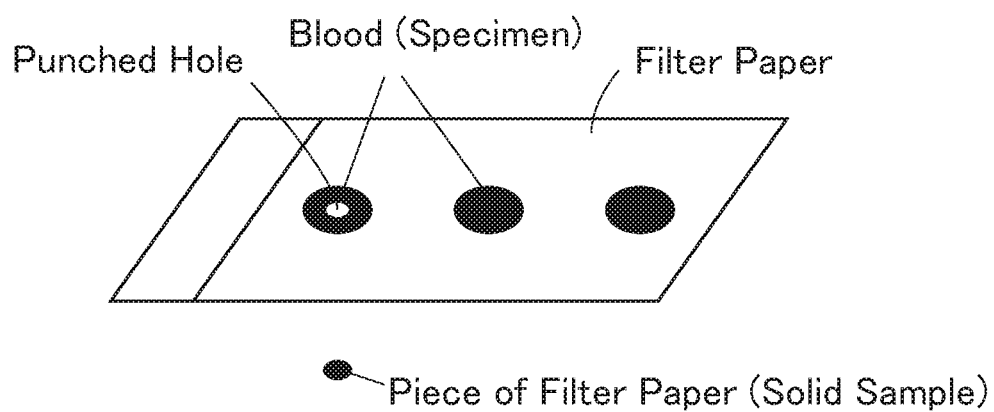
FIG. 3A is a schematic perspective view of an example of a solid sample.
Figure 3B:
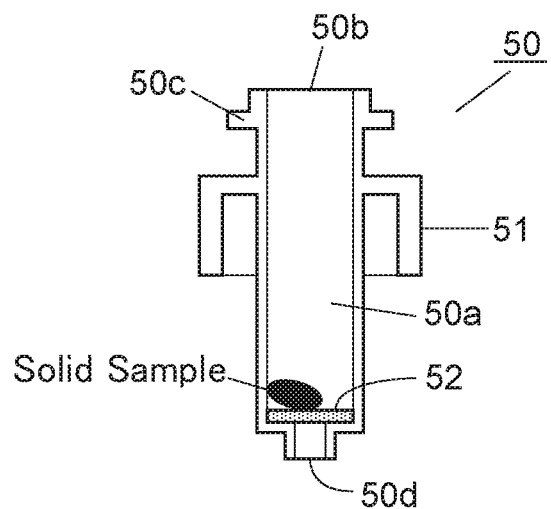
FIG. 3B is a diagram showing the separation device containing a solid sample.

Further, this embodiment is configured to allow the preprocessing container comprising the separation device 50 containing a solid sample and the collection container 54 to be set in the preprocessing container setting part 12. The solid sample refers to a sample in which a liquid (or a solidified liquid) as a specimen is held by a solid medium, such as apiece of filter paper shown in FIG. 3A which is obtained by cutting a specimen portion (or a portion containing at least a specimen) of filter paper impregnated with blood (specimen) to a predetermined size (e.g., 3 mm in diameter). As shown in FIG. 3B, such a solid sample is placed in the separation device 50, and the separation device 50 is set in the preprocessing container setting part 12 so that preprocessing such as extraction processing for extracting a specimen from the solid sample is automatically performed.

When setting the separation device 50 containing a solid sample in the preprocessing container setting part 12, an analyst inputs information about a specimen contained in the solid sample and the position of this separation device 50 set in the preprocessing container setting part 12 to the apparatus. When preprocessing is performed on the specimen, the apparatus identifies the position of the separation device 50 containing the specimen on the basis of the information input thereto and performs a preprocessing item designated by the analyst on the separation device 50. The details of preprocessing operations will be described later.

The separation device 50 and the collection container 54 constituting the preprocessing container will be described with reference to FIG. 2A, FIG. 2B, FIG. 2C, and FIG. 2D.

Figure 2A:
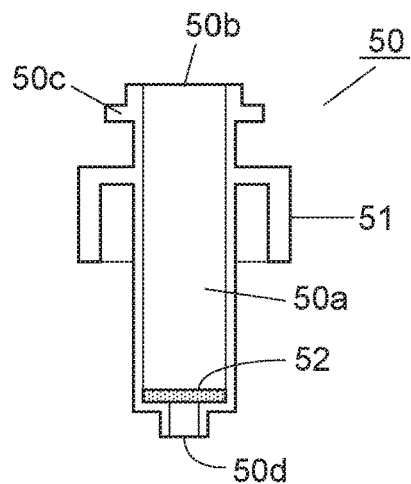
FIG. 2A is a cross-sectional view showing an example of a separation device of a preprocessing container.

As shown in FIG. 2A, the separation device 50 is a cylindrical container having an internal space 50a in which a specimen and a reagent are to be contained. A separating layer 52 is provided at the bottom of the internal space 50a. The separating layer 52 is a separating agent or a separating membrane having the function of selectively separating a specific component in a specimen by allowing the specimen to pass therethrough to allow the specific component to physically or chemically react therewith. Examples of the separating agent used to form the separating layer 52 include an ion-exchange resin, silica gel, cellulose, and activated carbon. Examples of the separating membrane to be used include a PTFE (polytetrafluoroethylene) membrane, a nylon membrane, a polypropylene membrane, a PVDF (polyvinylidene fluoride) membrane, an acrylic copolymer membrane, a mixed cellulose membrane, a nitrocellulose membrane, a polyethersulfone membrane, an ion-exchange membrane, and a glass fiber membrane.

Further, as a deproteinizing filter (separating membrane) for removing protein in a specimen by filtration, a PTFE membrane, an acrylic copolymer membrane, or the like can be used. In this case, in order to prevent clogging of the deproteinizing filter, as shown in FIG. 2D, a prefilter 52b may be provided above the deproteinizing filter 52a. As such a prefilter 52b, a nylon membrane, a polypropylene membrane, a glass fiber membrane, or the like can be used. The prefilter 52b is provided to remove insoluble matter and foreign matter having a relatively large particle diameter from a specimen, which makes it possible to prevent the deproteinizing filter 52a from being clogged with insoluble matter and foreign matter having a relatively large particle diameter.

The separation device 50 has an opening 50b provided in its upper surface to inject a specimen or a reagent and an extract outlet 50d provided in its lower surface to discharge a liquid that has passed through the separating agent 52. Further, the separation device 50 has a flange 50c provided on its upper outer circumferential surface, and the flange 50c circumferentially protrudes so as to be engaged with the holding part 25 of the carrying arm 24 that will be described later.

Below the flange 50c, a skirt 51 is provided so as to circumferentially protrude and then extend downward some distance to surround the outer circumferential surface of the separation device 50. As will be described later, the skirt 51 comes into close contact with the edge of a filtration port 30 of a processing part 28 when the separation device 50 is held in the filtration port 30 together with the collection container 54 so that an enclosed space is formed inside the skirt 51.

Figure 2B:
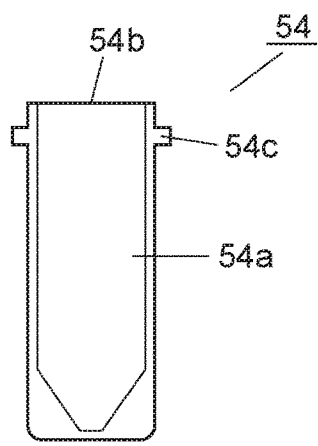
FIG. 2B is a cross-sectional view showing an example of a collection container of the preprocessing container.
Figure 2C:
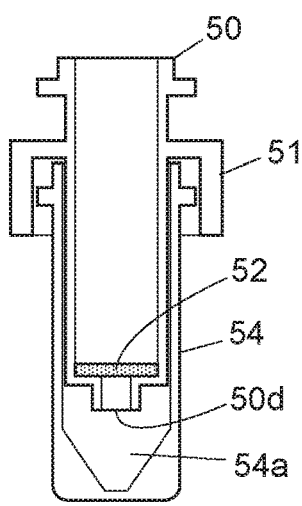
FIG. 2C is a cross-sectional view showing the preprocessing container in which the collection container is attached to the separation device.

As shown in FIG. 2B and FIG. 2C, the collection container 54 is a cylindrical container that holds the lower portion of the separation device 50 and collects an extract discharged through the extract outlet 50d of the separation device 50. The collection container 54 has, in its upper surface, an opening 54b through which the lower portion of the separation device 50 is to be inserted, and has an internal space 54a in which a portion of the separation device 50 located below the skirt 51 is to be held. Similarly to the separation device 50, the collection container 54 has a flange 54c provided on its upper outer circumferential surface, and the flange 54c circumferentially protrudes so as to be engaged with the holding part 25 of the carrying arm 24. The flange 54c has the same shape and outer diameter as the flange 50c of the separation device 50. The holding part 25 of the carrying arm 24 can hold the flange 50c of the separation device 50 and the flange 54c of the collection container 54 in the same manner.

When the collection container 54 is attached to the separation device 50, the upper portion of the collection container 54 enters inside the skirt 51. The outer diameter of the separation device 50 and the inner diameter of the collection container 54 are designed so that when the separation device 50 is held in the internal space 54a of the collection container 54, a slight clearance is created between the outer circumferential surface of the separation device 50 and the inner circumferential surface of the collection container 54. In the preprocessing container setting part 12, the preprocessing container 50 and the collection container 54 are set in a state where the lower portion of the separation device 50 is held in the collection container 54 (i.e., in a state shown in FIG. 2C).

The preprocessing apparatus 1 will be further described with reference to FIG. 1. As ports for holding the preprocessing containers and performing specific preprocessing items, filtration ports 30, stirring ports 36a, temperature-control ports 38 for separation device 50, and temperature-control ports 40 for collection container 54 are provided in a preprocessing part. The filtration ports 30 are provided in two positions on the inner side of the preprocessing container setting part 12. The three stirring ports 36a are provided in a stirring part 36 provided adjacent to the preprocessing container setting part 12. The temperature-control ports 38 and 40 are provided along an arc. A dilution port 41 is provided adjacent to the temperature-control ports 40.

The filtration ports 30 are connected to a negative-pressure applying mechanism 55 (see FIG. 4C and FIG. 5), and the negative-pressure applying mechanism 55 is configured to apply a negative pressure to the preprocessing container set in the filtration port 30. The filtration ports 30 and the negative-pressure applying mechanism 55 constitute the preprocessing part that performs the filtration of a specimen as preprocessing. The stirring part 36 also constitutes the preprocessing part. The stirring part 36 has a mechanism that periodically operates each of the stirring ports 36a in a horizontal plane individually to stir a specimen solution contained in the separation device 50 placed in each of the stirring ports 36a. The temperature-control ports 38 and 40 also constitute the preprocessing part. Each of the temperature-control ports 38 and 40 is provided in, for example, a heat-conductive block whose temperature is controlled by a heater and a Peltier element so that the separation device 50 or the collection container 54 held in the temperature-control port 38 or 40 is adjusted to a certain temperature.

The filtration port 30 will be described with reference to FIG. 4A, FIG. 4B, FIG. 4C, and FIG. 4D.

The filtration port 30 includes a recess in which the preprocessing container is to be held. As shown in FIG. 4D, the collection container 54 is first held in the filtration port 30, and then the lower portion of the separation device 50 is held in the internal space 54a of the collection container 54.

In the filtration port 30, a collection container holding member 31 is provided. The collection container holding member 31 evenly presses the collection container 54 from two opposite directions so as to sandwich the collection container 54 to center the collection container 54 (see FIG. 4B and FIG. 4D). The collection container holding member 31 is a U-shaped metal member that is upwardly open, and its two arms extending upwardly constitute two plate springs configured to be elastically displaced in the inner diameter direction of the filtration port 30. Each of the two plate springs of the collection container holding member 31 has a curved or bent shape that is inwardly curved or bent so that the distance between the two plate springs in a portion between the upper end and the lower end of the collection container holding member 31 is the smallest. The distance between the two plate springs at the upper end and lower end of the collection container holding member 31 is larger than the outer diameter of the collection container 54, and the smallest distance between the two plate springs is smaller than the outer diameter of the collection container 54. Since the collection container holding member 31 has such a shape, when the collection container 54 is inserted into the filtration port 30, the two plate springs of the collection container holding member 31 are opened as the collection container 54 comes down, and the collection container 54 is kept in the center of the filtration port 30 because of the elastic force of the plate springs. The collection container holding member 31 is fixed in the filtration port 30 so as not to be lifted up together with the collection container 54 when the collection container 54 is taken out of the filtration port 30.

A ring-shaped sealing member 60 having elasticity is provided at the edge of the upper opening of the filtration port 30. The sealing member 60 is fitted into a recess provided around the edge of the upper opening of the filtration port 30. The sealing member 60 is made of an elastic material such as silicone rubber or EPDM (ethylene-propylene-diene rubber). When the collection container 54 and the separation device 50 are set in the filtration port 30, the lower end of the skirt 51 of the separation device 50 abuts against the sealing member 60 so that a space surrounded by the inner side surface of the skirt 51 and the inner side surface of the filtration port 30 is hermetically sealed.

Figure 4A:
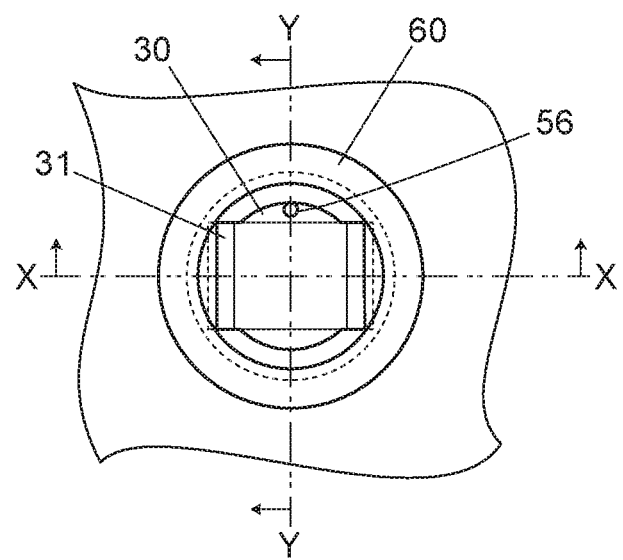
FIG. 4A is a plan view showing a filtration port.
Figure 4B:
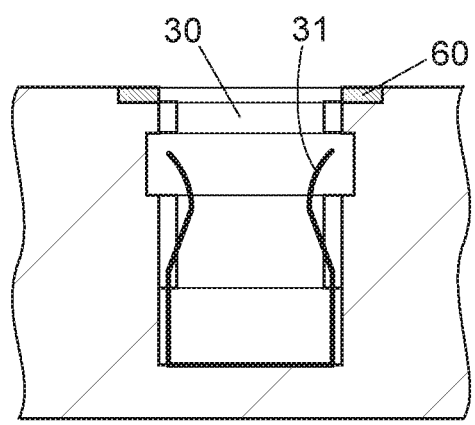
FIG. 4B is a cross-sectional view taken along a line X-X in FIG. 4A.
Figure 4C:
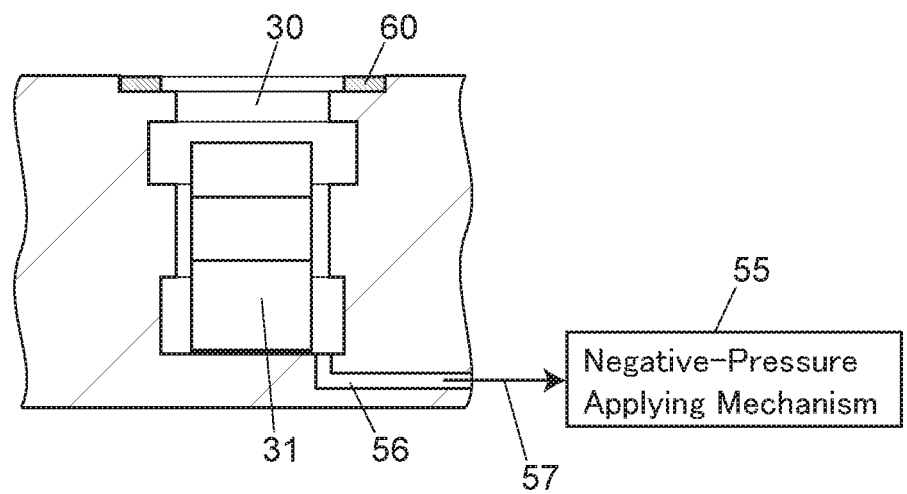
FIG. 4C is a cross-sectional view taken along a line Y-Y in FIG. 4A.
Figure 4D:
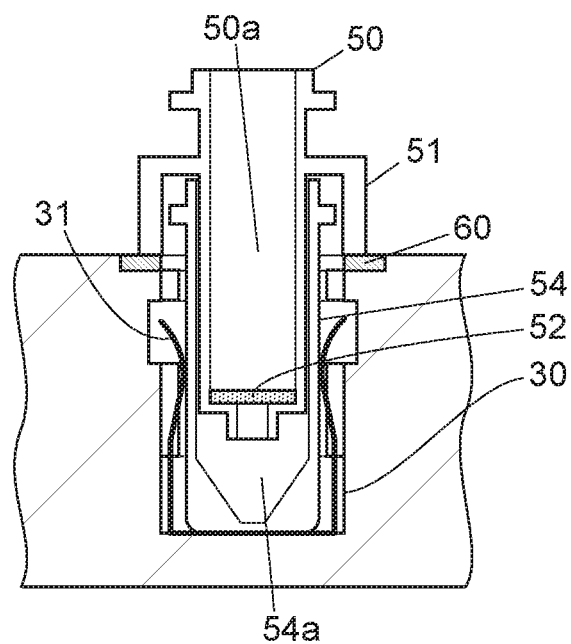
FIG. 4D is a sectional configuration diagram showing a state in which the preprocessing container is set in the filtration port.

The bottom surface of the filtration port 30 communicates with a flow path 56 for decompression (see FIG. 4A and FIG. 4C). The flow path 56 is connected to a flow path 57 of the negative-pressure applying mechanism 55. Although the specific configuration of the negative-pressure applying mechanism 55 will be described later, the negative-pressure applying mechanism 55 is designed to apply a negative pressure to the filtration port 30 with the use of a vacuum pump.

When the filtration port 30 is decompressed by the negative-pressure applying mechanism 55 with the separation device 50 and the collection container 54 being held in the filtration port 30, a negative pressure is caused in a space surrounded by the inner side surface of the skirt 51 and the inner side surface of the filtration port 30. The space in which a negative pressure is created communicates with the internal space 54a of the collection container 54. Since the upper surface of the separation device 50 is open to the atmosphere, a pressure difference is caused between the internal space 50a of the separation device 50 and the internal space 54a of the collection container 54 with the separating agent 52 being interposed therebetween so that only components, which can pass through the separating agent 52, of a sample solution contained in the internal space 50a of the separation device 50 are extracted and collected in the internal space 54a of the collection container 54 due to the pressure difference.

An example of the negative-pressure applying mechanism 55 is shown in FIG. 5.

The two filtration ports 30 are connected to a common vacuum tank 66. Each of the flow paths 57 that connects each of the filtration ports 30 to the vacuum tank 66 includes a pressure sensor 62 and a three-way valve 64. The pressure sensor 62 senses the pressure of the filtration port 30. The three-way valve 64 can select any one of a state where the filtration port 30 is connected to the vacuum tank 62, a state where the filtration port 30-side end of the flow path 57 is open to the atmosphere (i.e., a state shown in FIG. 5), and a state where the filtration port 30-side end of the flow path 57 is sealed.

The vacuum tank 66 is connected to a pressure sensor 68, and is connected also to a vacuum pump 58 through a three-way valve 70. Therefore, the vacuum tank 66 can be connected to the vacuum pump 58, if necessary, to adjust the pressure in the vacuum tank 66.

When extraction processing is performed on a specimen in any one of the filtration ports 30, the filtration port 30 is connected to the vacuum tank 66 to adjust a value sensed by the pressure sensor 62 that senses the pressure in the filtration port 30 to a predetermined value, and then the filtration port 30-side end of the flow path 57 is sealed. As a result, a sealed system is created in the filtration port 30 so that the inside of the filtration port 30 is kept decompressed to perform extraction processing on a specimen.

Figure 6A:
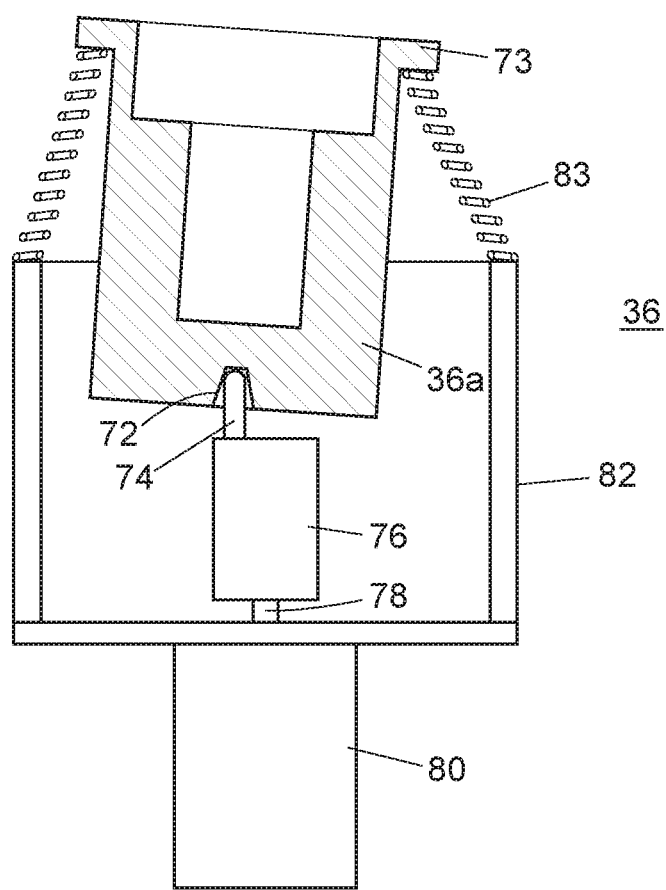
FIG. 6A is a sectional configuration diagram showing the structure of a stirring part.
Figure 6B:
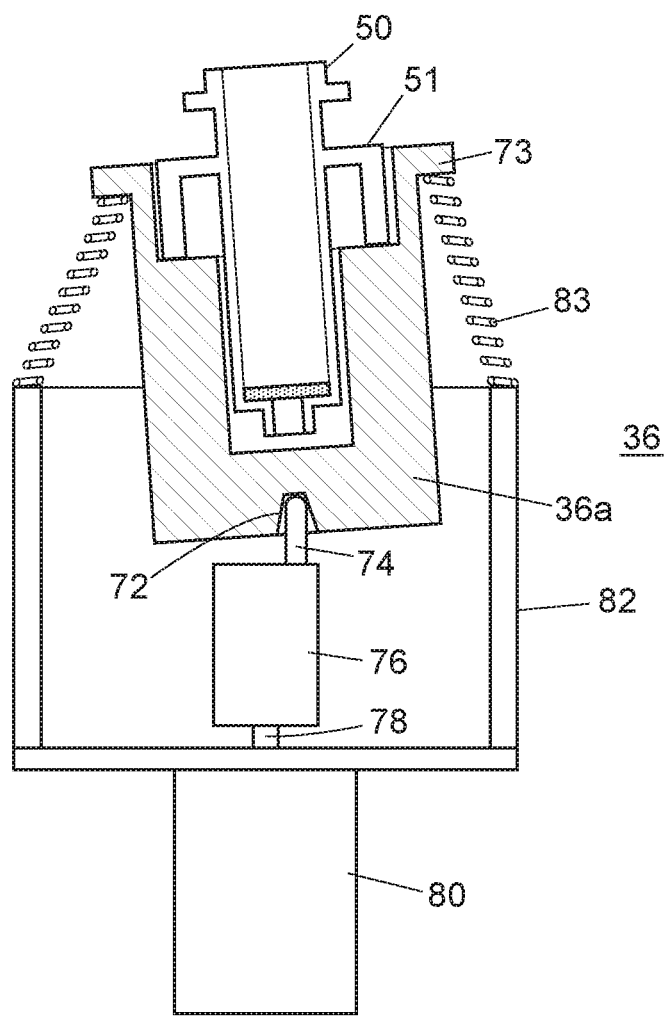
FIG. 6B is a sectional configuration diagram showing a state in which the stirring part is operated.

Hereinbelow, the structure of the stirring part 36 will be described with reference to FIG. 6A and FIG. 6B. FIG. 6A and FIG. 6B show one of the stirring ports 36a of the stirring part 36.

The stirring port 36a of the stirring part 36 is a container that holds the separation device 50. The stirring port 36a is driven by a stirring mechanism provided below the stirring port 36a.

The stirring mechanism that drives the stirring port 36a will be described. A rotor 76 is provided below the stirring port 36a, and a driving shaft 74 is vertically attached to the upper surface of the rotor 76 in a position displaced from the center of the rotor 76. The upper end of the driving shaft 74 is inserted into a supporting hole 72 provided in the lower surface of the stirring port 36a. The rotor 76 is supported by a rotating shaft 78 that is rotated by a motor 80. Therefore, the rotor 76 is rotated by driving the motor 80 so that the driving shaft 74 is turned in a horizontal plane.

A supporting frame 82 is attached to the motor 80. The supporting frame 82 has a side wall that extends vertically upward from the motor 80 side, and one end of an elastic member 83, such as a coil spring, is attached to the upper end of the side wall. The other end of the elastic member 83 is attached to the outer surface of the upper portion of the stirring port 36a to elastically hold the upper portion of the stirring port 36a. The elastic member 83 is provided in each of two or more positions (e.g., four positions) so that the elastic members 83 are evenly spaced around the stirring port 36a.

When the motor 80 is driven in a state where the separation device 50 containing a sample and a reagent is held in the stirring port 36a, as shown in FIG. 6B, the driving shaft 74 is turned in a horizontal plane so that the lower portion of the collection container 72 is turned. As a result, the specimen and the reagent contained in the separation device 50 held in the stirring port 36a are stirred and mixed.

Again referring to FIG. 1, the preprocessing apparatus 1 includes a sample transfer device 42 at the side edge of its housing. The sample transfer device 42 is provided to transfer an extracted sample collected in the collection container 54 to a sample injector (e.g., an automatic sampler) provided adjacent to the preprocessing apparatus 1. The sample transfer device 42 includes a moving part 44 that is moved by a driving mechanism having a rack and pinion mechanism in one direction (i.e., in a direction indicated by arrows in FIG. 1) in a horizontal plane. In the upper surface of the moving part 44, a transfer port 43 for setting the collection container 54 containing an extracted sample is provided.

While sample transfer to the sample injector is not performed, the transfer port 43 is placed in a position along the track of the holding part 25 of the carrying arm 24 (i.e., in a position indicated by a solid line in FIG. 1). In a state where the transfer port 43 is placed in such a position, setting of the collection container 54 in the transfer port 43 or collection of the collection container 54 from the transfer port 43 is performed by the carrying arm 24.

When specimen transfer to the sample injector is performed, the collection container 54 containing an extracted specimen is set in the transfer port 43, and then the moving part 44 is moved toward the outside of the preprocessing apparatus 1, and the transfer port 43 is placed in a position closer to the sample injector adjacent to the preprocessing apparatus 1 (i.e., in a position indicated by a dashed line in FIG. 1). In a state where the transfer port 43 is placed in such a position, a sampling nozzle provided in the sample injector sucks the specimen contained in the collection container 54. When the suction of the specimen by the sample injector is finished, the moving part 44 is returned to its original position (i.e., a position indicated by a solid line in FIG. 1), and the collection container 54 is collected by the carrying arm 24. The used collection container 54 is carried to a disposal port 34 and disposed of by the carrying arm 24.

The preprocessing apparatus 1 includes the disposal port 34 for disposing of the used separation device 50 and the used collection container 54. The disposal port 34 is provided in a position that is close to the dispensing port 32 and along the track of the holding part 25 of the carrying arm 24. Further, the preprocessing apparatus 1 includes a washing port 45 for washing the sampling nozzle 20a. The washing port 45 is provided in a position along the track of the sampling nozzle 20a. Although not shown in the drawing, a washing port for washing the probe 27 is provided in a position along the track of the probe 27.

Figure 7:
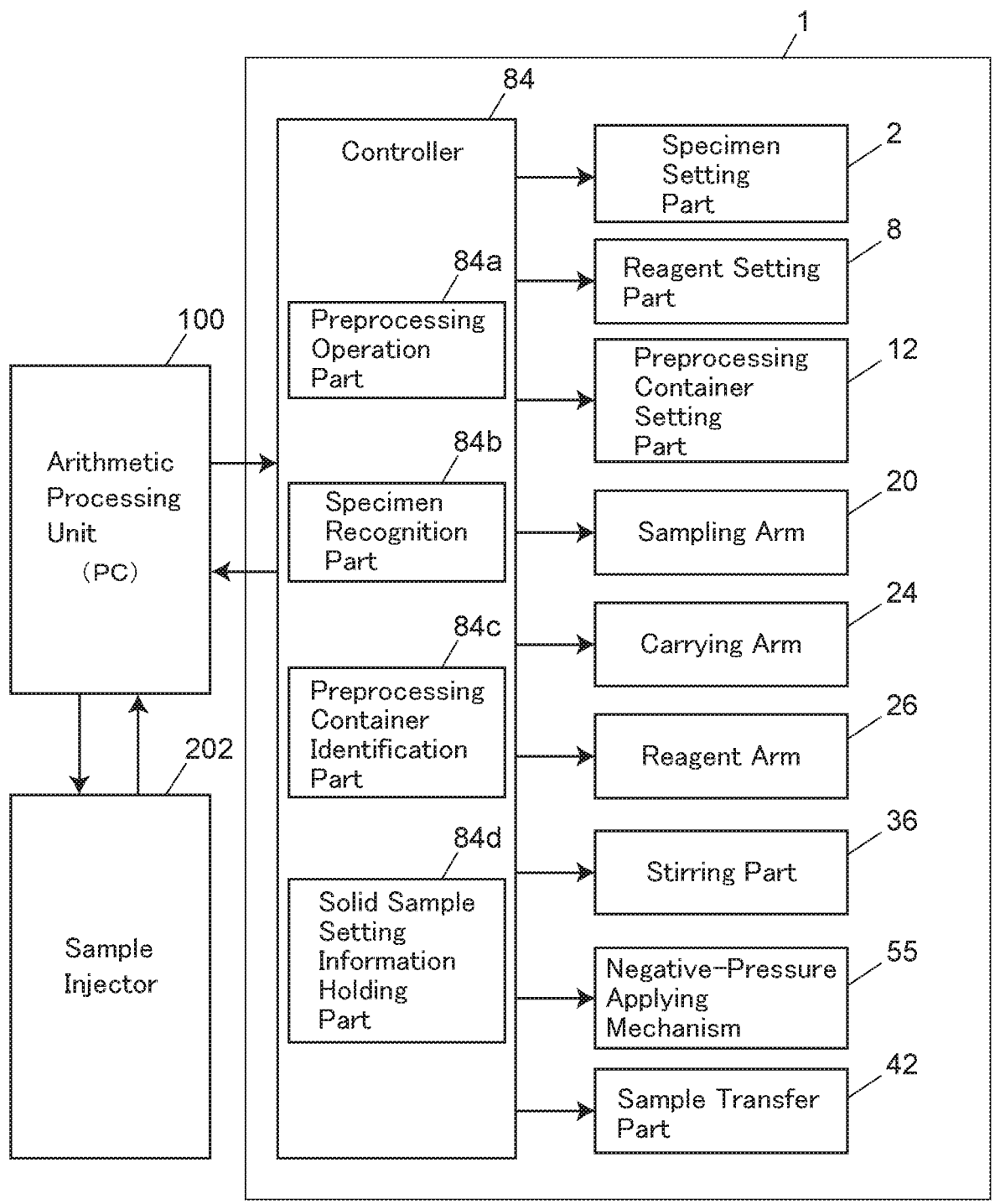
FIG. 7 is a block diagram showing a control system according to this embodiment.

Hereinbelow, the control system of the preprocessing apparatus 1 will be described with reference to FIG. 7. In the following description, the term "port" refers to any one of the filtration port 30, the dispensing port 32, the stirring port 36a, the temperature-control ports 38 and 40, and the transfer port 43 in which the separation device 50 or the collection container 54 is to be set.

The operations of the specimen setting part 2, the reagent setting part 8, the preprocessing container setting part 12, the sampling arm 20, the carrying arm 24, the reagent arm 26, the stirring part 36, the sample transfer device 42, and the negative-pressure applying mechanism 55 provided in the preprocessing apparatus 1 are controlled by a controller 84. The controller 84 is implemented by a computer provided in the preprocessing apparatus 1 and software executed by the computer. The controller 84 is connected to an arithmetic processing unit 86 implemented by, for example, a personal computer (PC) or a dedicated computer, and an analyst controls the preprocessing apparatus 1 through the arithmetic processing unit 86. The arithmetic processing unit 86 is electrically connected to a liquid chromatographic system (hereinafter referred to as "LC system") 200 (see FIG. 11 and FIG. 12) that is provided adjacent to the preprocessing apparatus 1 to analyze a sample that has been subjected to preprocessing in the preprocessing apparatus 1. A sample injector 202 provided in the LC system 200 is configured to operate in conjunction with the preprocessing apparatus 1. FIG. 7 shows only the sample injector 202 in the LC system 200.

The controller 84 includes a preprocessing operation part 84a, a specimen recognition part 84b, a preprocessing container identification part 84c, and a solid sample setting information holding part 84d. Each of the preprocessing operation unit 84a, the specimen recognition part 84b, and the preprocessing container identification part 84c is a function achieved by execution of software by an arithmetic element such as a CPU constituting the controller 84. Further, the solid sample setting information holding part 84d is a function achieved by the storage area of a storage device provided in a computer constituting the controller 84.

As described above, the preprocessing apparatus 1 according to this embodiment processes two kinds of specimens, one of which is a liquid specimen contained in the specimen container set in the specimen setting part 2 and the other of which is a specimen contained in a solid sample contained the separation device 50 set in the preprocessing container setting part 12. Information about a specimen to be analyzed is previously registered on the apparatus by an analyst. The controller 84 identifies a position where a specimen to be subjected to preprocessing next is set and a preprocessing item to be performed on the specimen on the basis of the registered information, and performs operations necessary for performing the preprocessing item.

The preprocessing operation part 84a is configured to confirm a processing item to be performed next on each specimen, check the availability of a port for performing the processing item, carry the separation device 50 containing the specimen or the collection container 54 to the port when the port is available, and perform the processing item. On the other hand, when there is no available port for performing the processing item, the target separation device 50 or collection container 54 is carried to the port as soon as the port becomes available.

The specimen recognition part 84b is configured to check whether a specimen to be analyzed is a liquid specimen or a specimen contained in a solid sample on the basis of previously-registered information. When the specimen recognition part 84b recognizes that a specimen to be analyzed is a liquid specimen, preprocessing operations for liquid specimen are performed. On the other hand, when the specimen recognition part 84b recognizes that a specimen to be analyzed is a specimen contained in a solid sample, preprocessing operations for solid sample are performed. Each of the preprocessing operations will be described later.

The preprocessing container identification part 84c is configured to, when the specimen recognition part 84b recognizes that a specimen to be analyzed is a specimen contained in a solid sample, identify the position of the preprocessing container (separation device 50) containing the solid sample on the basis of information about the specimen previously registered by an analyst. Information about a position where a solid sample is set is registered by an analyst and stored in the solid sample setting information holding part 84d when the separation device 50 containing the solid sample is set in the preprocessing container setting part 12.

Figure 8:
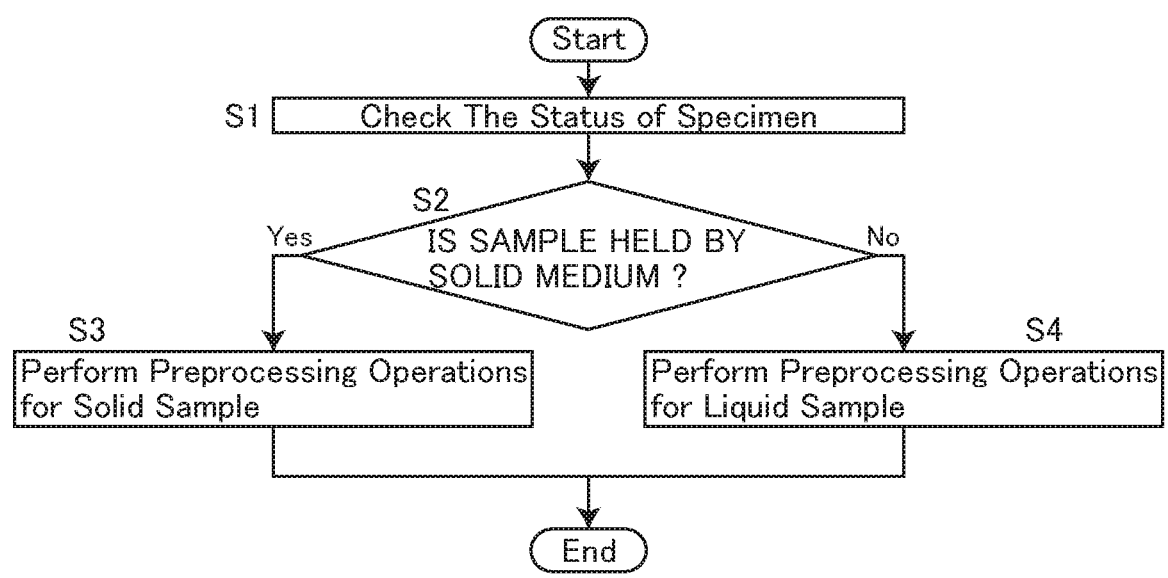
FIG. 8 is a flowchart showing an example of the operation of checking the state of a specimen before the start of preprocessing operations according to this embodiment.
Figure 9:
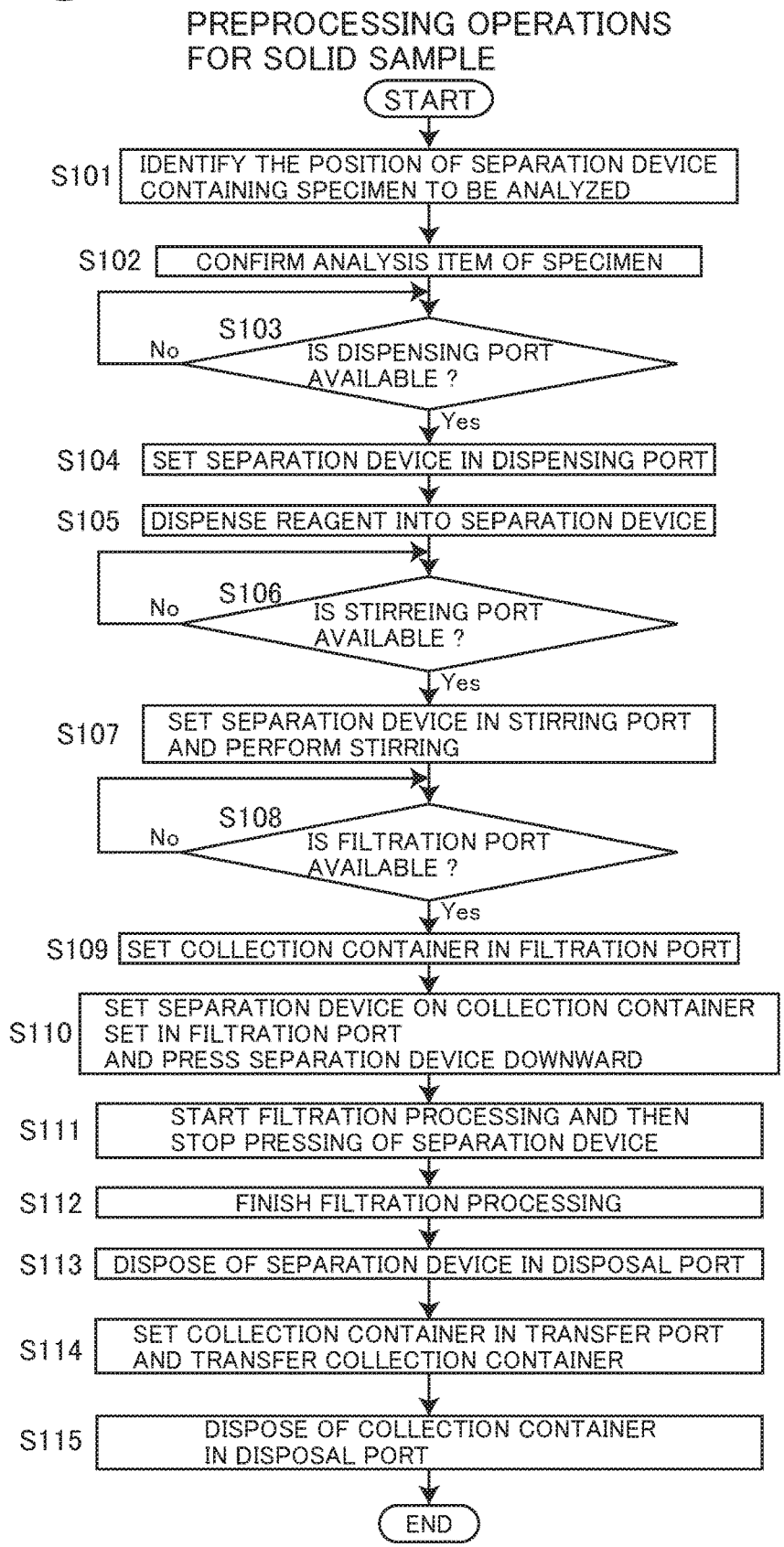
FIG. 9 is a flowchart showing an example of preprocessing operations for solid sample according to this embodiment.
Figure 10:
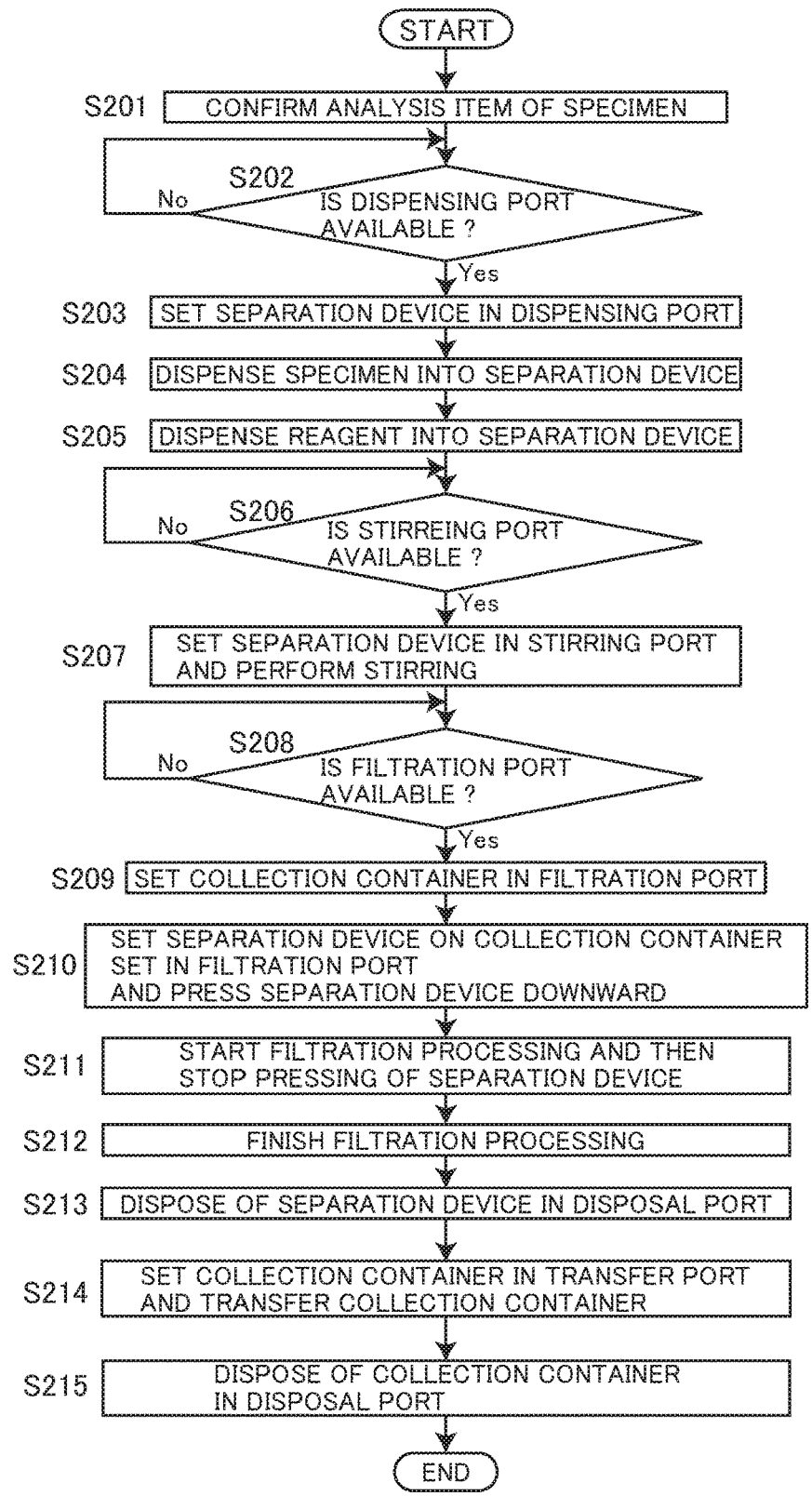
FIG. 10 is a flowchart showing an example of preprocessing operations for liquid specimen according to this embodiment.

An example of preprocessing operations performed on one sample according to this embodiment will be described with reference to FIG. 1 and flow charts shown in FIG. 8, FIG. 9, and FIG. 10. The flow charts shown in FIGS. 8 to 10 show only the flow of preprocessing performed on one specimen, and the operations of the preprocessing are performed in parallel with but independently of the operations of preprocessing performed on another specimen. "To perform preprocessing in parallel with but independently of" means that while filtration processing or stirring processing is performed on a certain specimen in the filtration port 30 or the stirring port 36a, the separation device 50 or collection container 54 containing another specimen is carried to another port by the carrying arm 24 to independently perform processing on the another specimen.

First, as shown in FIG. 8, the state of a specimen to be analyzed is checked, that is, it is checked whether a specimen to be analyzed is a liquid specimen or a specimen contained in a solid sample on the basis of information previously registered by an analyst (Step S1). When the specimen to be analyzed is a specimen contained in a solid sample (Step S2), preprocessing operations for solid sample are performed (Step S3). On the other hand, when the specimen to be analyzed is not a specimen contained in a solid sample, that is, when the specimen to be analyzed is a liquid specimen contained in the specimen container (Step S2), preprocessing operations for liquid specimen are performed (Step S4).

When the sample to be analyzed is a specimen contained in a solid sample, an example of preprocessing operations performed on the specimen is preprocessing operations for newborn mass screening. An example of such preprocessing operations will be described with reference to FIG. 9.

First, a position where the separation device 50 containing a solid sample containing a specimen to be analyzed is set is identified (Step S101), and an analysis item designated for the specimen is confirmed (Step S102).

Then, the availability of the dispensing port 32 is checked. When the dispensing port 32 is available, the separation device 50 containing a solid sample is taken out of the preprocessing container setting part 12 and set in the dispensing port 32 by the carrying arm 24 (Step S103 and Step S104). The separation device 50 and the collection container 54 are set in the preprocessing container setting part 12 in a state where they are stacked (i.e., in a state shown in FIG. 2). However, the carrying arm 24 holds only the separation device 50 stacked on the collection container 54 with the use of the holding part 25 and carries the separation device 50 to the dispensing part 32.

The reagent dispensing nozzle 26a takes a reagent for extracting the specimen from the solid sample from the reagent container 10 and dispenses the reagent into the separation device 50 set in the dispensing port 32 (Step S105). It is to be noted that a reagent dispensing port for dispensing a reagent may be provided in a position different from the position of the dispensing port 32 so that the separation device 50 is set in the reagent dispensing port by the carrying arm 24 to perform dispensing of a reagent in the position of the reagent dispensing port. An example of the reagent for specimen extraction is one obtained by dissolving stable isotopes (IS) of amino acids and acylcarnitines-32.

After the reagent for specimen extraction is dispensed into the separation device 50, the availability of the stirring port 36a is checked (Step S106). When the stirring port 36a is available, the separation device 50 set in the dispensing port 32 is carried and set in the available stirring port 36a by the carrying arm 24, and stirring is performed to extract the specimen from the solid sample (Step S107).

The stirring processing is preferably performed under a temperature condition of about 45° C. for about several tens of minutes. Therefore, the separation device 50, to which the reagent for specimen extraction has been added, is preferably carried to the temperature-control port 38 before the separation device 50 is carried to the stirring port 36a, that is, the separation device 50 is preferably carried to the stirring port 36a to perform stirring after the temperature of the separation device 50 is adjusted to about 45° C. Further, in order to stabilize the temperature of the separation device 50, the separation device 50, to which the reagent for specimen extraction has been added, may be alternately set in the temperature-control port 38 and the stirring port 36a to alternate temperature control and stirring.

The processing from addition of a reagent to stirring is extraction processing for extracting the specimen from the solid sample. During the extraction processing, the availability of the filtration port 30 is checked (Step S108). When the filtration port 30 is available, the collection container 54 is set in the filtration port 30 by the carrying arm 24 (Step S109). The collection container 54 set in the filtration port 30 is one paired with the separation device 50 that is being stirred in the stirring port 36a, that is, one that has been set in the preprocessing container setting part 12 with the separation device 50, which is being stirred, being stacked thereon. It is to be noted that during the stirring processing, the carrying arm 24 may carry the separation device 50 or the collection container 54 for another sample.

When the stirring processing (extraction processing) in the stirring part 36 is finished, the carrying arm 24 carries the separation device 50 to the filtration port 30 and sets the separation device 50 on the collection container 54 so that the lower portion of the separation device 50 is held in the collection container 54 set in the filtration port 30 (a state shown in FIG. 4, Step S110). At this time, the separation device 50 is pressed downward (i.e., toward the filtration port 30) so that the lower end of the skirt 51 of the separation device 50 comes down to a level slightly lower (e.g., about 0.1 mm) than the level of the upper surface of the sealing member 60 provided around the filtration port 30. As a result, the lower end of the skirt 51 of the separation device 50 compresses the sealing member 60, which improves air tightness between the lower end of the skirt 51 and the sealing member 60. The carrying arm 24 keeps pressing the separation device 50 downward until a negative pressure is caused in the filtration port 30 after the start of filtration processing that will be described below.

Filtration processing is started in a state where the separation device 50 is set on the collection container 54 set in the filtration port 30 and the filtration port 30 is hermetically sealed. In the filtration processing, the filtration port 30 is decompressed by the negative-pressure applying mechanism 55 so that a negative pressure is caused in the filtration port 30 holding the separation device 50 and the collection container 54. The filtration port 30 is kept at negative pressure for a certain period of time so that the solution contained in the separation device 50 is filtered and an extracted specimen is collected in the collection container 54 (Step S111).

When the pressure sensor 62 (see FIG. 5) senses that a negative pressure is caused in the filtration port 30 after the filtration processing is started, the carrying arm 24 stops pressing the separation device 50 downward and holding the separation device 50. After stopping of holding the separation device 50, the carrying arm 24 can carry another separation device 50 or collection container 54. The stopping of downward pressing of the separation device 50 and holding of the separation device 50, which are performed by the carrying arm 24, is not necessarily performed on the basis of the detection signal of the pressure sensor 62, and may be performed after predetermined time elapses from the start of the filtration processing.

After the filtration processing of the specimen is finished (Step S112), the three-way valve 64 (see FIG. 5) is switched to return the pressure in the filtration port 30 to atmospheric pressure, and the used separation device 50 is taken out of the filtration port 30 and disposed of in the disposal port 34 by the holding part 25 of the carrying arm 24 (Step S113). Then, the collection container 54 containing the filtered specimen is allowed to stand to allow a derivatization reaction of succinylacetone with hydrazine under acidic conditions to proceed. The time required for this processing is about several tens of minutes to 2 hours. This processing can be performed in the temperature-control port 40.

After the completion of the above processing, the availability of the transfer port 43 is checked. When the transfer port 43 is available, the collection container 54 is set in the transfer port 43 by the carrying arm 24. When the collection container 54 is set in the transfer port 43, the moving part 44 is moved to a position (i.e., a position indicated by a dashed line in FIG. 1) closer to the sample injector 202 provided in the LC system 200 (see FIG. 11 and FIG. 12) provided adjacent to the preprocessing apparatus 1 so that the collection container 54 is transferred to the sample suction device 90 (Step S114).

In the sample injector 202, the specimen contained in the collection container 54 transferred by the transfer device 42 is sucked by a sampling nozzle. The moving part 44 stops in the position closer to the LC system 200 until the suction of the specimen performed in the sample injector 202 is finished, and then the moving part 44 returns to its original position (i.e., a position indicated by a solid line in FIG. 1) when receiving a signal indicating that the suction of the specimen has finished from the LC system 200.

After the completion of sample transfer, the used collection container 54 is collected from the transfer port 43 and disposed of in the disposal port 34 by the carrying arm 24 (Step S115).

Hereinbelow, an example of preprocessing operations performed when a specimen to be analyzed is a liquid specimen will be described with reference to FIG. 10.

When a specimen to be analyzed is a liquid specimen, an analysis item previously designated by an analyst for the specimen is first confirmed (Step S201), and a preprocessing item necessary for performing the analysis item is determined. The availability of the dispensing port 32 is checked. When the dispensing port 32 is available, the carrying arm 24 takes the unused separation device 50 for containing the specimen out of the preprocessing container setting part 12 and sets the separation device 50 in the dispensing port 32 (Steps S202 and S203). As has been described above, the separation device 50 and the collection container 54 are set in the preprocessing container setting part 12 in a state where they are stacked (i.e., in a state shown in FIG. 2C), but also in this case, the carrying arm 24 holds only the separation device 50 stacked on the collection container 54 with the use of the holding part 25 and carries the separation device 50 to the dispensing part 32.

The sampling nozzle 20*a* dispenses the specimen into the separation device 50 (Step S204). After dispensing the specimen into the separation device 50, the sampling nozzle 20*a* is washed in the washing port 45 and prepared for dispensing of a next specimen. The reagent dispensing nozzle 26*a* takes a reagent appropriate to preprocessing to be performed on the specimen dispensed into the separation device 50 from the reagent container 10 and dispenses the reagent into the separation device 50 set in the dispensing port 32 (Step S205). It is to be noted that the dispensing of the reagent into the separation device 50 may be performed before the dispensing of the sample.

After the specimen and the reagent are dispensed into the separation device 50, the availability of the stirring port 36*a* is checked (Step S206). When the stirring port 36*a* is available, the separation device 50 set in the dispensing port 32 is carried and set in the available stirring port 36*a* by the carrying arm 24 to perform stirring (Step S207). This stirring processing is performed for a predetermined certain period of time to mix the specimen and the reagent contained in the separation device 50. During the stirring processing, the availability of the filtration port 30 is checked (Step S208). When the filtration port 30 is available, the collection container 54 is set in the filtration port 30 by the carrying arm 24 (Step S209).

When the stirring processing in the stirring part 36 is finished, the carrying arm 24 carries the separation device 50 to the filtration port 30 and sets the separation device 50 on the collection container 54 (a state shown in FIG. 4D), and further presses the separation device 50 downward (i.e., toward the filtration port 30) to improve air tightness between the lower end of the skirt 51 and the sealing member 60 (Step S210). The carrying arm 24 keeps pressing the separation device 50 downward until a negative pressure is caused in the filtration port 30 after the start of filtration processing that will be described below.

In a state where the separation device 50 is set on the collection container 54 set in the filtration port 30 and the filtration port 30 is hermetically sealed, the filtration port 30 is decompressed by the negative-pressure applying mechanism 55 to perform filtration processing. The filtration port 30 is kept at negative pressure for a certain period of time so that the solution contained in the separation device 50 is filtered and an extracted specimen is collected in the collection container 54 (Step S211).

When the pressure sensor 62 (see FIG. 5) senses that a negative pressure is caused in the filtration port 30 after the filtration processing is started, the carrying arm 24 stops pressing the separation device 50 downward and holding the separation device 50. After stopping of holding the separation device 50, the carrying arm 24 can carry another separation device 50 or collection container 54. The stopping of downward pressing of the separation device 50 and holding of the separation device 50, which are performed by the carrying arm 24, is not necessarily performed on the basis of the detection signal of the pressure sensor 62, and may be performed after predetermined time elapses from the start of the filtration processing.

Although not incorporated in the preprocessing operations, temperature treatment is sometimes incorporated in which the sample contained in the separation device 50 is kept at a given temperature for a certain period of time after the sample contained in the separation device 50 is stirred. In this case, after the completion of the stirring processing, the availability of the temperature control port 40 is checked. When the temperature control port 38 is available, the separation device 50 is set in the available temperature control port 38. After a lapse of a certain period of time, the separation device 50 is taken out of the temperature control port 38 and then set on the collection container 54 set in the filtration port 30.

After the completion of the filtration processing of the specimen (Step S212), the three-way valve 64 (see FIG. 5) is switched to return the pressure in the filtration port 30 to atmospheric pressure, and the used separation device 50 is taken out of the filtration port 30 and disposed of in the disposal port 34 by the holding part 25 of the carrying arm 24 (Step S213).

Then, the availability of the transfer port 43 is checked. When the transfer port 43 is available, the carrying arm 24 sets the collection container 54 in the transfer port 43 to transfer the specimen to the sample injector 202 (Step S214), and collects the used collection container 54 from the transfer port 43 to dispose of the used collection container 54 in the disposal port 34 (Step S215).

It is to be noted that after the completion of the filtration processing of the sample, temperature treatment is sometimes performed in which the extracted sample collected in the collection container 54 is kept at a certain temperature for a certain period of time. In this case, the availability of the temperature control port 40 is checked. When the temperature control port 40 is available, the collection container 54 is set in the available temperature control port 40. Then, after a lapse of a certain period of time, the collection container 54 is carried from the temperature control port 40 to the transfer port 43 to perform sample transfer.

Hereinbelow, a separation device 550 and a collection container 554 that can be used instead of the separation device 50 and the collection container 54 shown in FIG. 2A to FIG. 2D will be described with reference to FIG. 13A, FIG. 13B, FIG. 14A, and FIG. 14B. In the following description, differences between the separation device 50 and the separation device 550 and differences between the collection container 54 and the collection container 554 will be described.

Figure 13A:
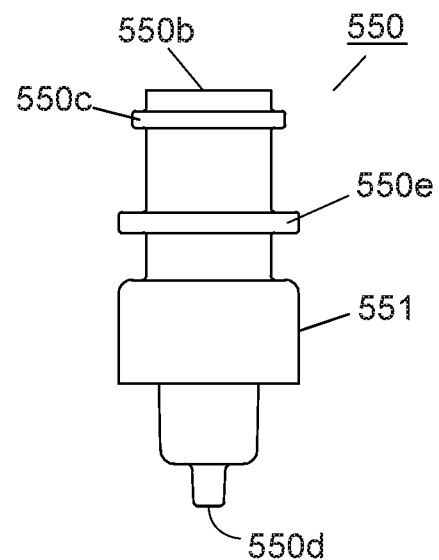
FIG. 13A is a front view showing another example of the separation device of the preprocessing container.
Figure 13B:
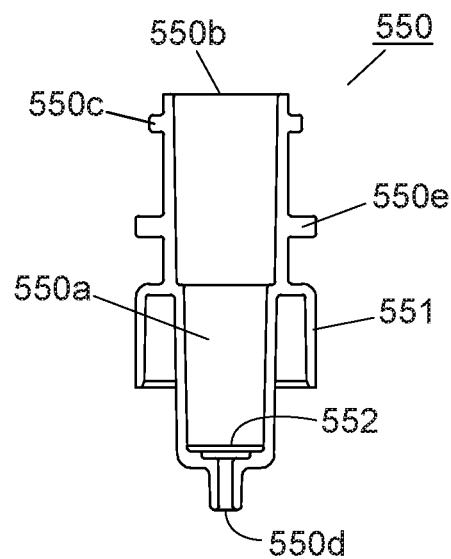
FIG. 13B is a cross-sectional view of the separation device shown in FIG. 13A.

In the separation device 550 shown in FIG. 13A and FIG. 13B, the inner diameter and outer diameter of a portion located below the base of a skirt 551 (i.e., a lower portion of the device) are smaller than those of a portion located above the base of the skirt 551. The lower portion of the device is to be held in a space 554a of the collection container 554. This allows a portion of the separation device 550 where a flange 550c is provided to have the same outer diameter as a portion of the collection container 554 where a flange 554c is provided. As a result, the flange 550c of the separation device 550 and the flange 554c of the collection container 554 can have completely the same shape and size, and therefore the holding part 25 of the carrying arm 24 can hold the separation device 550 and the collection container 554 in the same manner.

A protrusion 550e is provided between the flange 550c and the base of the skirt 551 on the outer circumferential surface of the separation device 550 so as to circumferentially protrude in the form of a flange like the flange 550c. The protrusion 550e is provided in a position such that the upper edge of the inner wall surface of the stirring port 36a is located when the separation device 550 is set in the stirring port 36a. The protrusion 550e has the same outer diameter as the skirt 551, which allows, when the stirring processing is performed, the protrusion 550e to abut against the upper edge of the inner wall surface of the stirring port 36a to prevent the vibration of the separation device 550 in the stirring port 36a.

Figure 14A:
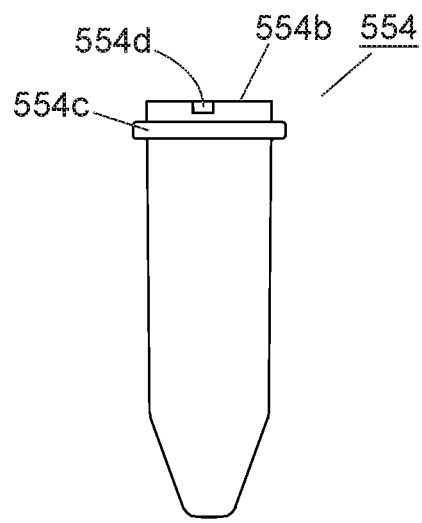
FIG. 14A is a front view showing another example of the collection container of the preprocessing container.
Figure 14B:
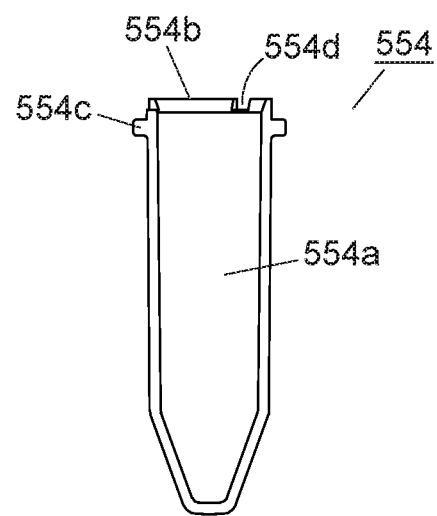
FIG. 14B is a cross-sectional view of the collection container shown in FIG. 14A.

In the collection container 554 shown in FIG. 14A and FIG. 14B, notches 554d are provided in two or more (e.g., three) positions at the edge of an upper opening 554b. The notches 554d form openings for the ventilation of air between the inner wall surface of the base of the skirt 551 and the upper edge of the collection container 554 when the separation device 550 and the collection container 554 are integrated with each other so that the upper portion of the collection container 554 enters the inside of the skirt 551 of the separation device 550. The filtration processing in the filtration port 30 is performed by sucking air in the filtration port 30 to cause a negative pressure in the collection container 554 integrated with the separation device 550 and set in the filtration port 30. At this time, air in the collection container 554 passes through the openings formed by the notches 554d so that the collection container 554 is efficiently decompressed.

Figure 11:
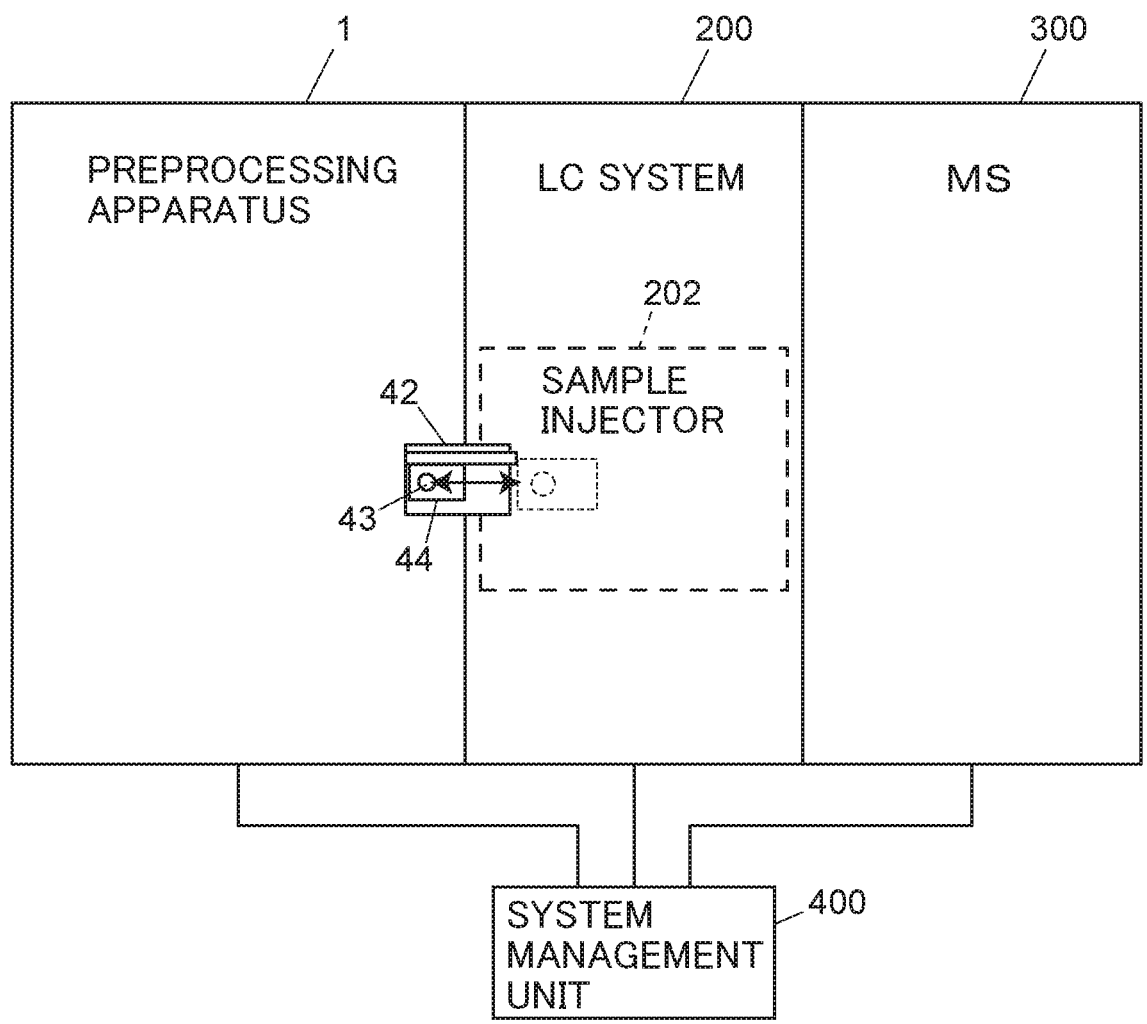
FIG. 11 is a block diagram schematically showing an embodiment of an analysis system.

Hereinbelow, an embodiment of an analysis system including the preprocessing apparatus 1 will be described with reference to FIG. 11.

An LC system 200 is provided adjacent to the preprocessing apparatus 1 described with reference to the above embodiment, and a mass spectrometer (MS) 300 is further provided adjacent to the LC system 200. The operations of the preprocessing apparatus 1, the LC system 200, and the MS 300 are managed by a common system management unit 400. The system management unit 400 is a dedicated computer or a general-purpose personal computer that includes software for controlling or managing the preprocessing apparatus 1, the LC system 200, and the MS 300, and also has the function of the arithmetic processing unit 100 shown in FIG. 7.

The LC system 200 includes the sample injector 202 that takes a specimen that has been subjected to preprocessing in the preprocessing apparatus 1 and injects the specimen into the analytical flow path of a liquid chromatograph. As has been described above, the preprocessing apparatus 1 includes the transfer device 42 that transfers the collection container 54 (or 554) containing a specimen that has been subjected to preprocessing to the LC system 200, and the sample injector 202 is configured to take the specimen from the collection container 54 (or 554) transferred to the LC system 200 by the transfer device 42. When the moving part 44 of the transfer device 42 is moved toward the LC system 200, the collection container 54 (or 554) set in the transfer port 43 of the moving part 44 is placed in a predetermined position in the sample injector 202.

When the collection container 54 (or 554) containing a specimen that has been subjected to preprocessing in the preprocessing apparatus 1 is set in the transfer port 43 of the transfer device 42, and the moving part 44 is moved toward the LC system 200 so that the collection container 54 (or 554) is placed in a predetermined position in the sample injector 202, a signal indicating this is sent to the sample injector 202 through the system management unit 400, and the sample injector 202 starts taking the specimen from the collection container 54 (or 554). The transfer device 42 keeps the collection container 54 (or 554) in a predetermined position in the sample injector 202 until the sample injector 202 finishes taking the specimen as a sample. When the sample injector 202 finishes taking the specimen as a sample, a signal indicating this is sent to the preprocessing apparatus 1 through the system management unit 400 so that the transfer device 42 moves the moving part 44 toward the preprocessing apparatus 1 to return the collection container 54 (or 554) to a predetermined position in the preprocessing apparatus 1. The collection container 54 (or 554) returned to the preprocessing apparatus 1 is carried to the disposal port 34 and disposed of by the carrying arm 24.

Figure 12:
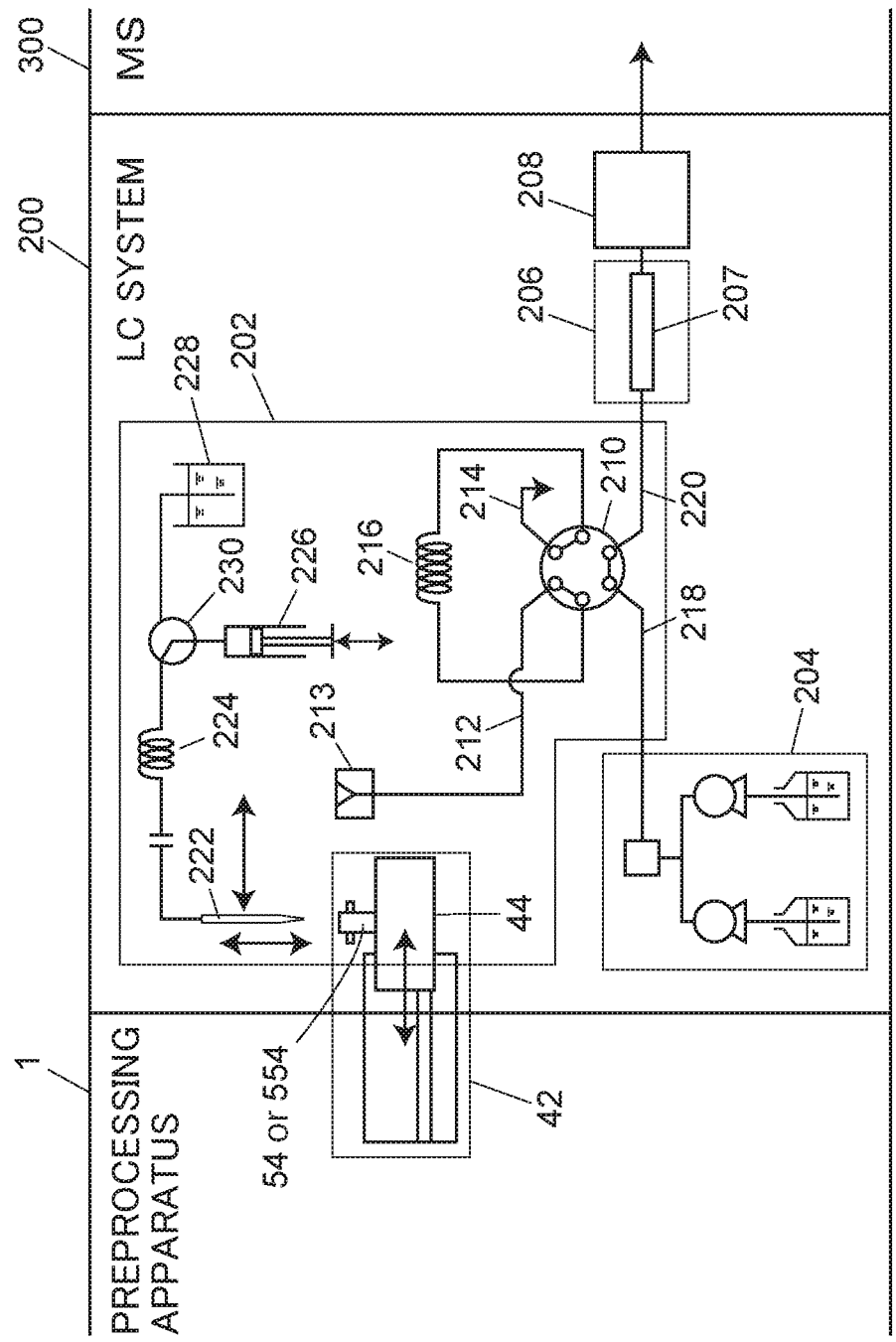
FIG. 12 is a flow path configuration diagram showing the configuration of a liquid chromatographic system according to this embodiment.

The LC system 200 according to this embodiment will be described with reference to FIG. 12.

The LC system 200 includes, in addition to the sample injector 202, a liquid sending device 204, a column oven 206, and a detector 208. The liquid sending device 204 is a device that sends, for example, two kinds of solvents with the use of liquid sending pumps to a mixer and sends a solution obtained by mixing them with the mixer as a mobile phase. The column oven 206 has an analytical column 207 that separates a sample (a specimen that has been subjected to preprocessing) into individual components. The detector 208 is a detector such as an ultraviolet absorption detector that detects sample components separated by the analytical column 207.

The liquid sending device 204 is located at the upstream end of an upstream analytical flow path 218 to send a mobile phase through the upstream analytical flow path 218. The analytical column 207 and the detector 208 are provided on a downstream analytical flow path 220. Both the upstream analytical flow path 218 and the downstream analytical flow path 220 are connected to ports of a two-position valve 210 provided in the sample injector 202, and are therefore connected to each other through the two-position valve 210.

The two-position valve 210 of the sample injector 202 have 6 ports. The ports of the two-position valve 210 are connected not only to the upstream analytical flow path 218 and the downstream analytical flow path 220 but also to a sample introduction flow path 212, a drainage flow path 214, and one end and the other end of a sample loop 216. They are configured so that one of the following states (1) and (2) can be selected by switching the two-position valve 210: (1) a state where the sample introduction flow path 212, the sample loop 216, and the drainage flow path 214 are connected in series so that the downstream end of the upstream analytical flow path 218 is directly connected to the downstream analytical flow path 220 (i.e., a state shown in FIGS. 12) and (2) a state where the upstream analytical flow path 218, the sample loop 216, and the downstream analytical flow path 220 are connected in series. The sample introduction flow path 212 communicates with an injection port 213.

The sample injector 202 has a needle 222 that can inject and discharge a liquid from its tip and a syringe pump 226 connected to the needle 222 through a flow path. The needle 222 is configured to be horizontally and vertically moved by a driving mechanism not shown in the drawing, and therefore can take a sample from the collection container 54 (or 554) transferred to the LC system 200 by the transfer device 42 and inject the sample through the injection port 213. The syringe pump 226 is configured to be connected also to a washing liquid container 228 that stores a washing liquid by switching a flow path switching valve 230. The inner surfaces of a sample loop 224, the needle 222, and the sample introduction flow path 212 can be washed by sending the washing liquid from the syringe pump 226 containing the washing liquid sucked thereinto in a state where the syringe pump 228 is connected to the needle 222 and the needle 222 is connected to the injection port 213.

When a specimen contained in the collection container 54 (or 554) is taken as a sample, the tip of the needle 22 is inserted into the collection container 54 (or 554), the syringe pump 226 sucks the sample, and the sample is held in the sample loop 224 provided between the needle 222 and the syringe pump 226. The sample held in the sample loop 224 is injected through the injection port 213. When the sample is injected through the injection port 213, the two-position valve 210 is operated to select the state (1) where the sample introduction flow path 212, the sample loop 216, and the drainage flow path 214 are connected in series so that the sample injected through the injection port 213 is held in the sample loop 216. Then, the two-position valve 210 is switched to select the state (2) where the upstream analytical flow path 218, the sample loop 216, and the downstream analytical flow path 220 are connected in series so that the sample held in the sample loop 216 is introduced into the analytical column 207 by a mobile phase sent by the liquid sending device 204 and separated into individual components by the analytical column 207. The individual components separated by the analytical column 207 are detected by the detector 208 and then further introduced into the MS 300.

Signals obtained by the detector 208 and the MS 300 are input into the system management unit 400 (see FIG. 11) and arithmetic processing such as quantitative determination and composition analysis of individual components separated by the analytical column 207 is performed by software installed in the system management unit 400 and hardware, such as a CPU, that executes the software.

What is claimed is:

1. A method for preprocessing of specimens using preprocessing containers before analyzing, wherein the method comprising the following steps of:
   a specimen preparing step for preparing specimens in a liquid state or in a state contained in a solid medium, a setting step, for setting in a state where a specimen can be dispensed into the preprocessing container when it is determined a specimen is in the liquid state, and for setting in a state where the solid medium holding a specimen is contained in the preprocessing container when it is determined the specimen is contained in the solid medium;

an information registration step for causing an analyst to register information regarding whether a specimen to be analyzed is in the liquid state or is contained in the solid medium;

a specimen recognition step for recognizing whether a specimen to be analyzed is in the liquid state or is contained in the solid medium on the basis of the information registered by the analyst;

a dispensing step for dispensing, when it is determined the specimen to be analyzed is in the liquid state, the specimen into the preprocessing container which is empty;

an extraction step for performing an extraction processing for extracting, when it is determined the specimen to be analyzed is contained in the solid medium, the specimen from the solid medium into the preprocessing container, which has been containing the solid medium; and a preprocessing step for performing predetermined preprocessing operation to the specimen dispensed into the preprocessing container by the dispensing step or to the specimen extracted into the preprocessing container by the extraction step;

an extraction port preparing step for preparing a plurality of extraction ports for performing the extraction processing;

a searching step for searching, after the specimen recognition step, when it is determined the specimen to be analyzed is contained in the solid medium, an available extraction port for performing the extraction processing, wherein in the extraction step, the extraction processing is performed at the available extraction port searched by the searching step; and when it is determined there are a plurality of specimens which are contained in the solid mediums, the extraction processing of each specimen is performed in parallel using the available extraction port different from each other.

2. The method according to claim 1, wherein in the information registration step, causing the analyst to register information about a position where the preprocessing container containing a solid medium holding a specimen when it is determined the specimen is contained in the solid medium, wherein the method further comprising a preprocessing container identification step for identifying the preprocessing container containing the solid medium holding the specimen to be analyzed on a basis of the information registered by the analyst; and a carrying step for carrying the preprocessing container identified by the preprocessing container identification step to the available extraction port, wherein the extraction step is performed after the carrying step.

3. The method according to claim 1, wherein the method is further comprising a transferring step for transferring the preprocessing container containing a specimen to be analyzed to a liquid chromatographic system after the preprocessing step.

* * * * *